United States Patent [19]

Hansenne et al.

[11] Patent Number: 5,605,679
[45] Date of Patent: Feb. 25, 1997

[54] PHOTOPROTECTIVE/COSMETIC COMPOSITIONS COMPRISING AT LEAST ONE SOLID ORGANIC SUNSCREEN COMPOUND AND DIPHENYLACRYLATE SOLVENT THEREFOR

[75] Inventors: Isabelle Hansenne; Victoria Van Leeuwen, both of Paris, France

[73] Assignee: L'Oreal, Paris, France

[21] Appl. No.: 463,762

[22] Filed: Jun. 5, 1995

[30] Foreign Application Priority Data

Jun. 3, 1994 [FR] France ................... 94 06833

[51] Int. Cl.⁶ ................. A61K 7/42; A61K 7/40
[52] U.S. Cl. ................. 424/59; 424/60; 424/401; 514/844; 514/938
[58] Field of Search .................. 424/59, 60, 401; 514/844, 938

[56] References Cited

FOREIGN PATENT DOCUMENTS 0005182  11/1979  European Pat. Off. .
0518772  12/1992  European Pat. Off. .
9111989   8/1991  WIPO .

OTHER PUBLICATIONS

Shaath, N. "Encyclopedia of UV Absorbers for Sunscreen Products" Cosmetie & Toiletries, vol. 102, Mar. 1987 pp. 21–36.

Rolandts, R. et al "A Survey of ultraviolet Absorbers in Commercialty available Sun Products", International Journal of Dematology May 1983, vol. 22, pp. 247–255.

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise (i) a photoprotecting effective amount of 4-methylbenzylidenecamphor and, optionally, of 4-(tert-butyl)-4'-methoxydibenzoylmethane and (ii) a 2-ethylhexyl α-cyano-β,β-diphenylacrylate sunscreen solvent, in an amount sufficient to substantially completely dissolve the total amount of the sunscreen constituent (i), in a cosmetically acceptable vehicle, diluent or carrier therefor.

25 Claims, No Drawings

PHOTOPROTECTIVE/COSMETIC COMPOSITIONS COMPRISING AT LEAST ONE SOLID ORGANIC SUNSCREEN COMPOUND AND DIPHENYLACRYLATE SOLVENT THEREFOR

CROSS-REFERENCE TO COMPANION APPLICATIONS

Copending applications Ser. No. 08/463,221, Ser. No. 08/463,505, Ser. No. 08/463,503 U.S. Pat. No. 5,489,431, Ser. No. 08/463,304, Ser. No. 08/463,508, Ser. No. 08/461, 015, Ser. No. 08/463,507 and Ser. No. 08/464,940 each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, typically an oil-in-water emulsion, combinatory immixture of (i) at least one particular solid lipophilic organic sunscreen compound and (ii) a particular liquid lipophilic diphenylacrylate sunscreen compound that solubilizes said at least one solid sunscreen compound (i) therein.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

One organic sunscreen compound having desirable properties and which to date has been widely used is 4-methylbenzylidenecamphor, which is commercially available and marketed under the trademark "EUSOLEX 6300" by Merck.

This is a lipophilic sunscreen compound, which is highly active in the UV-B range, but which presents the disadvantage of being solid at room temperature. For this reason, incorporating same into sunscreen/cosmetic compositions entails certain constraints as regards its formulation and application, in particular in the selection of the solvents permitting proper dissolution thereof. In this respect, solvent oils are typically employed, such as esters and in particular $C_{12}$–$C_{15}$ alkyl benzoates ("Finsolv TN" marketed by Finetex), or triglycerides and in particular triglycerides of $C_8$–$C_{12}$ fatty acids ("Miglyol 812" marketed by Hüls), or, alternatively, of monoalcohols or polyols such as ethanol, or mixtures thereof. These oils nevertheless present certain disadvantages, in particular they exhibit no specific (or intrinsic) activity in respect of screening UV radiation (whether UV-A and/or UV-B), even though their solubilizing properties vis-a-vis the aforesaid sunscreen camphor compound are adequate.

SUMMARY OF THE INVENTION

It has now unexpectedly and surprisingly been determined that 2-ethylhexyl α-cyano-β,β-diphenylacrylate (also known more simply as "octocrylene") is a conspicuously very good solvent for the solid sunscreen compound indicated above, namely, for 4-methylbenzylidenecamphor. Indeed, this solid lipophilic sunscreen compound exhibits extremely high solubilities in the aforesaid diphenylacrylate compound, which solubilities are, in all instances, markedly superior than those obtained using the other conventional solvents to date characterizing the state of this art. It is thus possible, with an equal amount of solvent, to formulate greater amounts of the solid camphor compound.

It should also be appreciated that 2-ethylhexyl α-cyano-β,β-diphenylacrylate is a liquid lipophilic screening compound already known to be active in the UV-B range, but its solubilizing properties in respect of the above solid sunscreen camphor compound have never been described.

Thus, the advantages of the present invention are manifold in that not only can the 4-methylbenzylidenecamphor be solubilized in a novel solvent, itself per se advantageous, but also, at the same time, a substantial increase is provided, at an equal concentration of the aforesaid sunscreen camphor compound in the final sunscreen/cosmetic composition, in the level of photoprotection imparted thereby.

It has also now been found that 2-ethylhexyl α-cyano-β, β-diphenylacrylate, or octocrylene, is not only an excellent solvent with respect to 4'-methylbenzylidenecamphor, which is active in the UV-B range, but also in respect of mixtures thereof with the solid lipophilic sunscreen compound 4-(tert-butyl)-4'-methoxydibenzoylmethane, which is active the in the UV-A range. Thus, improved sunscreen/cosmetic formulations are hereby provided which offer maximum photoprotection over the entire harmful UV range (280 nm–400 nm), and these formulations are moreover perfectly stable.

Briefly, the present invention features novel photoprotective/cosmetic compositions comprising, in a cosmetically acceptable vehicle, diluent or carrier, (i) an effective sunscreen amount of 4-methylbenzylidenecamphor and, optionally, of 4-(tert-butyl)-4'-methoxydibenzoylmethane, and (ii) an amount of the solvent 2-ethylhexyl α-cyano-β,β-diphenylacrylate to effectively solubilize the total amount of solid sunscreen compounds (i) contained therein.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

This invention, thus, also features the use of 2-ethylhexyl α-cyano-β,β-diphenylacrylate as a solvent in sunscreen/cosmetic compositions comprised of 4-methylbenzylidenecamphor and, optionally, of 4-(tert-butyl)-4'-methoxydibenzoylmethane.

DETAILED DESCRIPTION OF BEST MODE AND PREFERRED EMBODIMENTS OF THE INVENTION

More particularly according to the present invention, as indicated above, 4-methylbenzylidenecamphor (compound A to be solubilized) is a sunscreen compound that is per se known to this art and is active in the UV-B range, is a solid material and is marketed commercially under the trademark "EUSOLEX 6300" by Merck and under the trademark "PARSOL 5000" by Givaudan. This compound has the following structural formula (I):

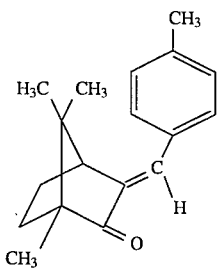

Similarly the 4-(tert-butyl)-4'-methoxydibenzoylmethane (optional compound B to also be solubilized) is a solid sunscreen compound active in the UV-A range and is also per se known to this art; it too is available commercially under the trademark "PARSOL 1789" by Givaudan. This compound B has the following structural formula (II):

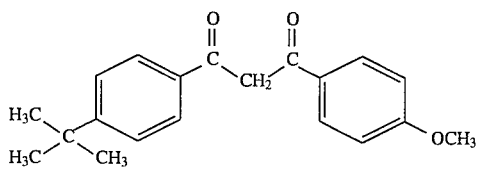

Also as indicated above, 2-ethylhexyl α-cyano-β,β-diphenylacrylate (solvent compound C), i.e., octocrylene, is a liquid lipophilic sunscreen compound that is per se known to this art for its activity in the UV-B range. This too is a commercially available compound, marketed under the trademark "UVINUL N. 539" by BASF. It has the following structural formula (III):

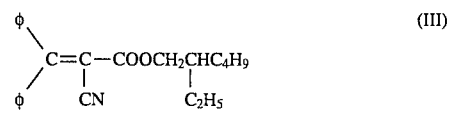

in which φ is a phenyl radical.

The compound A (solid UV-B sunscreen compound to be solubilized) is advantageously present in the sunscreen/cosmetic compositions according to the invention at a concentration ranging from 0.5% to 10% by weight relative to the total weight of the composition. In an essential embodiment of the present invention, the compound A must exist in the final sunscreen/cosmetic composition in a totally, or substantially totally, solubilized (dissolved) state.

The compound C (solubilizing agent) is itself advantageously present in the sunscreen/cosmetic compositions according to the invention at a concentration ranging from 2% to 15% by weight relative to the total weight of the composition. In a particularly preferred and advantageous embodiment of the invention, the compound C is employed in an amount sufficient to itself dissolve the total amount, or substantially the total amount, of the compound A present in the composition.

A determination of the solubility parameters, carried out at room temperature, of the compound A in the compound C indicates that the solubilization conditions described above are attained when the [(compound C)/(compound A)] weight ratio ranges from 0.3 to 30. This ratio preferably is above 0.5 and below 25, and even more preferably is below 10. For example, the solubility of the compound A in the compound C is on the order of 60% by weight.

When the compound B (solid UV-A sunscreen compound) is formulated into the sunscreen/cosmetic compositions in accordance with the invention, it should then also be present therein in a totally, or substantially totally solubilized (dissolved) state. In this event, the amount of compound B should remain compatible (namely, capable of being dissolved on the one hand, and, on the other, without effecting destabilization or any other perturbation) with the phase comprising the [(compound A)+(compound C)] admixture, or an amount of compound C is initially employed which is sufficient to provide complete and stable dissolution of the [(compound A)+(compound B)] mixture. A mixture comprising compound A and compound B in a 3:1 weight ratio, for example, is soluble in a proportion of approximately 55% by weight in the solvent compound C.

Moreover, the concentrations and ratios of the compounds A, optionally B and C are typically selected such that the sun protection factor of the final composition is preferably at least 2.

In another particularly preferred embodiment of the invention, the final sunscreen/cosmetic compositions preferably contain no, or substantially no, solubilizing agent for the compounds A or (A+B) other than the solvent compound C described above. According to the invention, a given compound is considered as not possessing any solubilizing properties with respect to another given compound when the latter compound has a solubility of less than approximately 1% by weight in the first compound.

In another preferred embodiment of the present invention, the cosmetically acceptable vehicle, diluent, carrier or support in which the various compounds A, optionally B and C are formulated is an emulsion of oil-in-water type.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or, alternatively, nanopigments (average size of the primary particles: generally ranging from 5 nm to 100 nm, preferably from 10 to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all photoprotective agents that are per se well known to this art and which are effective by physical blocking (reflection and/or diffusion) of the UV irradiation. Conventional coating agents include, moreover, alumina and/or aluminum stearate. Such coated or uncoated metal oxide nanopigments are described, in particular, in EP-A-0,518,772 and EP-A-0,518,773.

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, α-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-α-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, J. Mol. Biol, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, a styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation. If desired, the fatty phase of the emulsions according to the invention may comprise only or essentially only the diphenylacrylate C (organic solvent/sunscreen) in which the compounds A and, optionally, B are dissolved, together with the optional additional screening agents and other conventional lipophilic cosmetic additives and adjuvants.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

Oil-in-water emulsion:

| | | |
|---|---|---|
| (a) | 4-Methylbenzylidenecamphor ("EUSOLEX 6300") | 3 g |
| (b) | 2-Ethylhexyl α-cyano-β,β-diphenylacrylate ("UVINUL N 539") | 6 g |
| (c) | Mixture of cetylstearyl alcohol and oxyethylenated cetylstearyl alcohol containing 33 moles of ethylene oxide, marketed under the trademark "SINNOWAX AO" by Henkel (emulsifying agent) | 7 g |
| (d) | Mixture of glyceryl mono-, di- and tristearate (coemulsifying agent) | 2 g |
| (e) | $C_8$–$C_{12}$ fatty acid triglycerides ("MIGLYOL 812") | 2 g |
| (f) | Polydimethylsiloxane | 1.5 g |
| (g) | Cetyl alcohol | 1.5 g |
| (h) | Distilled water | qs 100 g |

The above emulsion was prepared by dissolving the photoprotective/sunscreen agents into the fatty phase and then by adding the (co)emulsifying agents into this fatty phase, heated to about 80° C., and, lastly, adding the water, preheated to this same temperature, with rapid stirring.

EXAMPLE 2

Oil-in-water emulsion:

| | | |
|---|---|---|
| (a) | 4-Methylbenzylidenecamphor ("EUSOLEX 6300") | 4.5 g |
| (b) | 4-(tert-butyl)-4'-methoxydibenzoylmethane ("PARSOL 1789") | 1.5 g |
| (c) | 2-Ethylhexyl α-cyano-β,β-diphenylacrylate ("UVINUL N539") | 10 g |
| (d) | Mixture of cetylstearyl alcohol and oxyethylenated cetylstearyl alcohol containing 33 moles of ethylene oxide, marketed under the trademark "SINNOWAX AO" by Henkel (emulsifying agent) | 7 g |
| (e) | Mixture of glyceryl mono-, di- and tristearate (coemulsifying agent) | 2 g |
| (f) | $C_8$–$C_{12}$ fatty acid triglycerides ("MIGLYOL 812") | 2 g |
| (g) | Polydimethylsiloxane | 1.5 g |
| (h) | Cetyl alcohol | 1.5 g |
| (i) | Distilled water | qs 100 g |

The above emulsion was prepared as in Example 1.

EXAMPLE 3

Water-in-oil emulsion:

| | | |
|---|---|---|
| (a) | 4-Methylbenzylidenecamphor ("EUSOLEX 6300") | 3 g |
| (b) | 4-(tert-butyl)-4'-methoxydibenzoylmethane ("PARSOL 1789") | 1 g |
| (c) | 2-Ethylhexyl α-cyano-β,β-diphenylacrylate ("UVINUL N539") | 8 g |
| (d) | $TiO_2$ of nanopigment grade | 1.5 g |
| (e) | [Glyceryl and sorbitol hydroxystearate and isostearate] mixture containing 20 moles of propylene oxide and 30 moles of ethylene oxide, marketed under the trademark "ARLACEL 780" by ICI | 2 g |
| (f) | Preservatives | qs |
| (g) | Fragrance | qs |
| (h) | Distilled water | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising (i) a photoprotecting effective amount of 4-methylbenzylidenecamphor and, optionally, of 4-(tert-butyl)-4'-methoxydibenzoylmethane and (ii) a 2-ethylhexyl α-cyano-β,β-diphenylacrylate sunscreen solvent, in an amount sufficient to substantially completely dissolve the total amount of the sunscreen constituent (i), in a cosmetically acceptable vehicle, diluent or carrier therefor.

2. The sunscreen/cosmetic composition as defined by claim 1, comprising (i) a photoprotecting effective amount of a mixture of said 4-methylbenzylidenecamphor compound and said 4-(tert-butyl)-4'-methoxydibenzoylmethane compound.

3. The sunscreen/cosmetic composition as defined by claim 1, substantially devoid of any solvent for said sunscreen constituent (i), other than said 2-ethylhexyl α-cyano-β,β-diphenylacrylate solvent (ii).

4. The sunscreen/cosmetic composition as defined by claim 1, comprising from 0.5% to 10% by weight of said 4-methylbenzylidenecamphor sunscreen compound.

5. The sunscreen/cosmetic composition as defined by claim 4, comprising from 2% to 15% by weight of said 2-ethylhexyl α-cyano-β,β-diphenylacrylate solvent (ii).

6. The sunscreen/cosmetic composition as defined by claim 1, wherein the ratio by weight [(2-ethylhexyl α-cyano-β,β-diphenylacrylate)/4-methylbenzylidenecamphor)] ranges from 0.3 to 30.

7. The sunscreen/cosmetic composition as defined by claim 6, said ratio by weight being greater than 5.

8. The sunscreen/cosmetic composition as defined by claim 7, said ratio by weight being less than 25.

9. The sunscreen/cosmetic composition as defined by claim 8, said ratio by weight being less than 10.

10. The sunscreen/cosmetic composition as defined by claim 1, comprising an oil-in-water emulsion.

11. The sunscreen/cosmetic composition as defined by claim 1, comprising a water-in-oil emulsion.

12. The sunscreen/cosmetic composition as defined by claim 1, further comprising at least one additional hydrophilic or lipophilic organic UV-A and/or UV-B sunscreen.

13. The sunscreen/cosmetic composition as defined by claim 12, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

14. The sunscreen/cosmetic composition as defined by claim 1, further comprising a photoprotecting effective amount of particulates of at least one inorganic pigment or nanopigment.

15. The sunscreen/cosmetic composition as defined by claim 14, said at least one pigment or nanopigment comprising titanium dioxide, zinc oxide, iron oxide, zirconium oxide, cerium oxide, or mixture thereof.

16. The sunscreen/cosmetic composition as defined by claim 1, further comprising at least one active agent for the artificial tanning and/or browning of human skin.

17. The sunscreen/cosmetic composition as defined by claim 1, further comprising at least one cosmetically acceptable adjuvant or additive.

18. The sunscreen/cosmetic composition as defined by claim 17, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

19. The sunscreen/cosmetic composition as defined by claim 1, comprising a nonionic vesicle dispersion, emulsion, cream, milk, gel, cream gel, ointment, suspension, dispersion, powder, solid stick, foam or spray.

20. The sunscreen/cosmetic composition as defined by claim 1, comprising a makeup.

21. The sunscreen/cosmetic composition as defined by claim 20, comprising an anhydrous or aqueous solid or paste, emulsion, suspension, or dispersion.

22. The sunscreen/cosmetic composition as defined by claim 1, comprising a shampoo, lotion, gel, emulsion, nonionic vesicle dispersion, hair lacquer, or rinse.

23. The sunscreen/cosmetic composition as defined by claim 1, having a sun protection factor of at least 2.

24. A method for protecting human skin and/or hair against the deleterious effects of ultraviolet irradiation, comprising topically applying thereto an effective amount of the sunscreen/cosmetic composition as defined by claim 1.

25. A method for protecting human skin and/or hair against the deleterious effects of solar radiation, comprising topically applying thereto an effective amount of the sunscreen/cosmetic composition as defined by claim 1.

* * * * *